US008082162B2

(12) United States Patent
Flood (10) Patent No.: US 8,082,162 B2
(45) Date of Patent: *Dec. 20, 2011

(54) MEDICAL IMPLANT VERIFICATION CARD (76) Inventor: Mark Andrus Flood, Fountain Hills, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/657,545

(22) Filed: Jan. 22, 2010

(65) Prior Publication Data

US 2010/0127075 A1 May 27, 2010

Related U.S. Application Data (62) Division of application No. 10/369,254, filed on Feb. 18, 2003, now Pat. No. 7,676,385.

(51) Int. Cl.
*G06Q 10/00* (2006.01)
*G06Q 50/00* (2006.01)
*G06Q 40/00* (2006.01)

(52) U.S. Cl. .................................... 705/3; 705/2; 705/4

(58) Field of Classification Search .................... 705/2–4
See application file for complete search history.

(56) References Cited

U.S. PATENT DOCUMENTS

| 5,423,334 | A | * | 6/1995 | Jordan | 128/899 |
| 5,635,012 | A | * | 6/1997 | Belluci et al. | 156/277 |
| 6,073,106 | A | * | 6/2000 | Rozen et al. | 705/3 |
| 6,434,531 | B1 | * | 8/2002 | Lancelot et al. | 705/3 |
| 6,480,745 | B2 | * | 11/2002 | Nelson et al. | 607/60 |
| 2001/0031998 | A1 | * | 10/2001 | Nelson et al. | 607/60 |
| 2001/0039504 | A1 | * | 11/2001 | Linberg et al. | 705/3 |
| 2004/0003522 | A1 | * | 1/2004 | Sachdev | 40/360 |

OTHER PUBLICATIONS

K. Johnson, et al., "Surgical Implants Complicate Screening for Security, Passengers", Airports. New York: Jan. 15, 2002. vol. 19, Iss. 3; p. 5.*

* cited by examiner

*Primary Examiner* — Jason Dunham
*Assistant Examiner* — Amber Altschul
(74) *Attorney, Agent, or Firm* — David O. Simmons

(57) ABSTRACT

A medical implant verification card (MIVC) having information provided on one or both sides thereof. Information for enabling access to a Medical Implant Verification Account (MIVA) of a patient is one the card. An image showing a medical implant as implanted within a body of the patient (e.g., reproduction of an x-ray image) is on the card. An image of an actual implant operation scar of the patient is on the card. The implant operation scar image shows a scar on the body of the patient resulting from implantation of the medical implant within the body of the patient. Implant identification information designating a type of the medical implant is on the card. Information designating a name of a surgeon having performed the operation for implanting the medical implant and/or information for contacting the surgeon is on the card.

18 Claims, 6 Drawing Sheets

MEDICAL IMPLANT VERIFICATION CARD

CROSS REFERENCE TO RELATED APPLICATIONS

This patent application is a divisional patent application claiming priority from U.S. Non-Provisional patent application having Ser. No. 10/369,254, filed 18-Feb. 2003, now U.S. Pat. No. 7,676,385 entitled "Methods And Equipment Adapted For Verifying Presence Of A Medical Implant Within A Patient", having a common applicant herewith and being incorporated herein in its entirety by reference.

FIELD OF THE DISCLOSURE

The disclosures herein relate generally to medical data and, more particularly, to identification cards configured with medical data.

BACKGROUND OF THE DISCLOSURE

There are many situations in which it is desirable, if not mandatory, to verify presence of a medical implant within a patient. One example of such a situation is when a metal detector detects presence of a medical implant in a person. As sensitivity of metal detection systems continues to increase and as metal detectors continue to proliferate into areas where they were typically not used previously, it will become more important for a medical implant recipient to verify the presence of a medical implant to law enforcement personnel, security personnel and other authorized personnel requesting such verification.

Commercial theft detection devices are also becoming more sensitive and sophisticated. Accordingly, in some instances, certain types of theft detection devices detect a person with a medical implant rather than a shoplifter. In such instances, it may be necessary for the person with the medical implant to readily verify presence of the medical implant.

Patient identification cards are one example of a conventional means for enabling presence of a medical implant to be verified (i.e., a conventional patient identification card). Conventional patient identification cards are limited in their effectiveness for several reasons. One limitation of conventional patient identification cards is that their issuance is often unrestricted (i.e., anyone can get a card). Another limitation is that they are typically not linked to an on-line verification database. Still another limitation is that they typically depict generic representations of a medical implant rather than the actual implant of a cardholder.

Implanted identification transponders are another example of a conventional means for enabling a medical implant to be verified. Implanted identification transponders mandate the use of a transponder reader and may present privacy issues stemming from unauthorized reading of such transponders. Furthermore, implanted identification transponders are themselves implanted devices that may require verification of presence.

Therefore, methods and equipment adapted for verifying presence of a medical implant within a patient in a manner that overcomes limitations associated with conventional methods and equipment adapted for verifying presence of a medical implant within a patient would be useful.

DETAILED DESCRIPTION OF THE DRAWING FIGURES

The disclosures made herein relate to various aspects of methods and equipment adapted for verifying presence of a medical implant within a patient (e.g., a person). Such methods and equipment, which are in accordance with embodiments of the disclosures made herein, are adapted for overcoming limitations associated with conventional methods and equipment providing related functionality. An objective of such methods and equipment as disclosed herein is to provide a remotely accessible, secure and trusted means for verifying presence of a medical implant within the patient.

One embodiment of the disclosures made herein is a Medical Implant Verification System (MIVS), which includes a Medical Implant Verification Card (MIVC). The MIVS is adapted for providing verification of the presence of a permanent medical implant within a patient to requesting parties such as airport security personnel, law enforcement personnel, military personnel, government agency personnel, doctors, hospital personnel, commercial security personnel, the patient and/or the patient's designee. Although the MIVS is specifically adapted for medical implants, it is contemplated herein that the MIVS may also be used for verifying non-medical implant items in a patient (e.g., retained bullet/shrapnel fragments).

A MIVS in accordance with an embodiment of the disclosures made herein provides an authorized requesting party with immediate access to information required for verifying presence of a medical implant in a medical implant patient. For example, in the case where the MIVS is accessible remotely via the Internet, access may be made available 24 hours per day, 7 days per week. In this manner, such a MIVS will be useful in a variety of situations. (e.g., verifying a medical implant in a airline passenger, verifying a medical implant in a shopper when they set off a retail store metal detector, verifying an implant in a person requesting access to a highly-classified area of a facility, etc).

By nature, certain medical implants are intended for being installed permanently (i.e., permanent medical implants). However, permanent medical implants do not always last a lifetime. Accordingly, the MIVS may be very useful to subsequent treating doctors, if removal or replacement of a permanent medical implant becomes necessary. The MIVS is a means for readily obtaining patient-specific information and implant-specific information.

Removal instruments for a particular medical implant are often unique to a manufacturer of that particular medical implant. Therefore, implant-specific information (e.g., identification of the exact make and/or model of the medical implant, implant removal information, etc.) in combination with other patient-specific information (e.g., the patient's blood type, allergies of the patient, etc.) may be imperative to safely and efficiently removing a particular medical implant. Such implant-specific information can usually be obtained from the implanting physician or from a patient's hospital. However, in a trauma situation, a means for readily accessing implant-specific information is vital when there is not enough time to obtain previous medical records from typical sources.

Furthermore, there has been national debate at the National Institute of Health (NIH) about an implant retrieval program. The MIVS disclosed herein provides a platform for patients who want to be identified as a voluntary implant donor for the purposes of implant retrieval and analysis. Similarly, the MIVS disclosed herein also provides a means for effectively facilitating product recall of medical implants. Many patients do not know the manufacturer of their implant or the name of their implant. Information such as the make and/or model of the patient's medical implant may be accessed via the MIVS disclosed herein.

Figure 1:
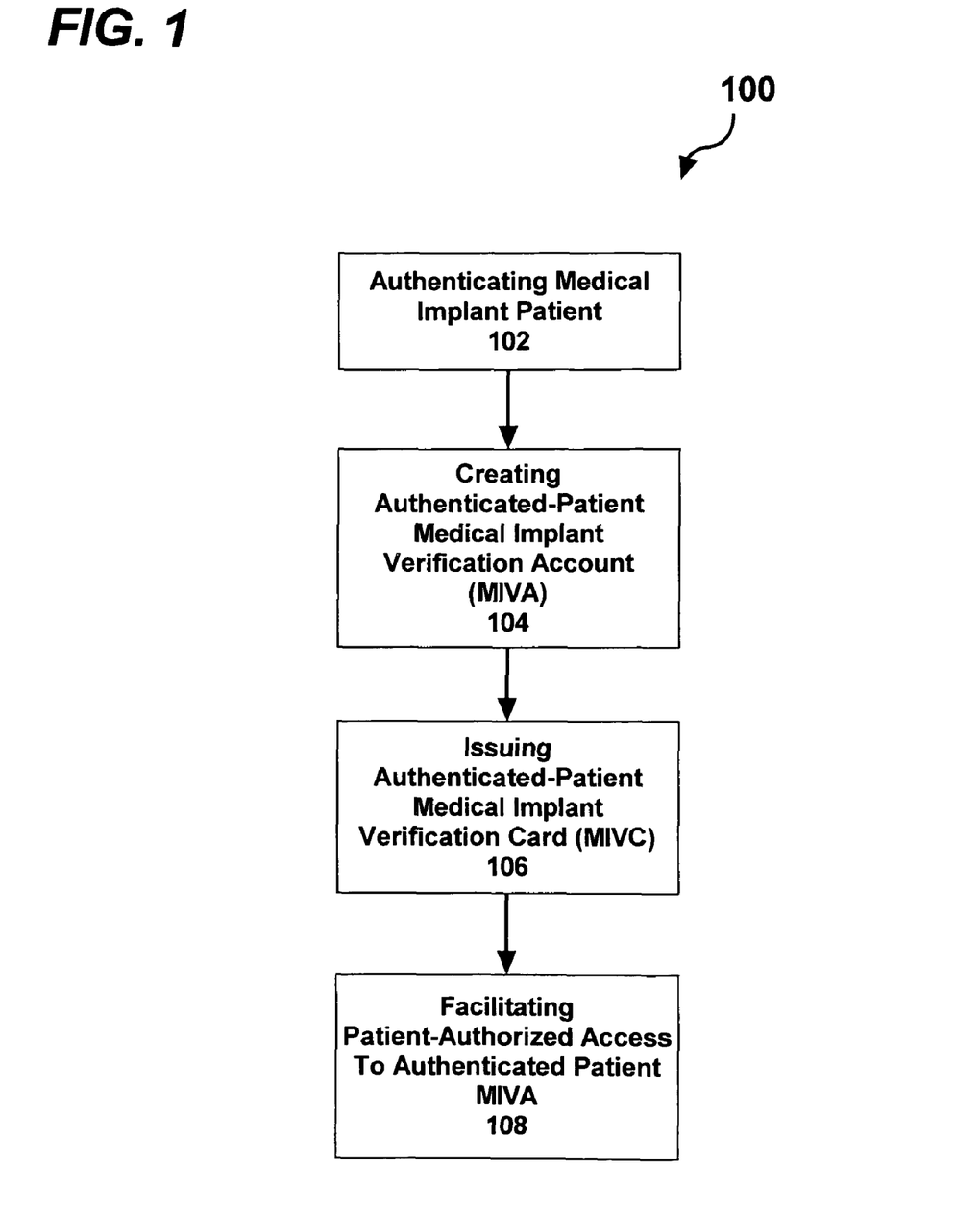
FIG. 1 depicts a method for verifying presence of a medical implant within a patient in accordance with an embodiment of the disclosures made herein.

Turning now to specific figures, FIG. 1 depicts a method 100 for verifying presence of a medical implant within a patient in accordance with an embodiment of the disclosures made herein. The method 100 includes an operation 102 for authenticating a medical implant patient. After successfully authenticating the medical implant patient, an operation 104 is performed for creating an authenticated-patient Medical Implant Verification Account (MIVA) for the medical implant patient. An operation 106 for issuing an authenticated-patient MIVC is performed after creating the authenticated-patient MIVA. Once the authenticated-patient MIVC is issued, an operation 108 is performed for facilitating patient-authorized access to the MIVA.

Figure 2:
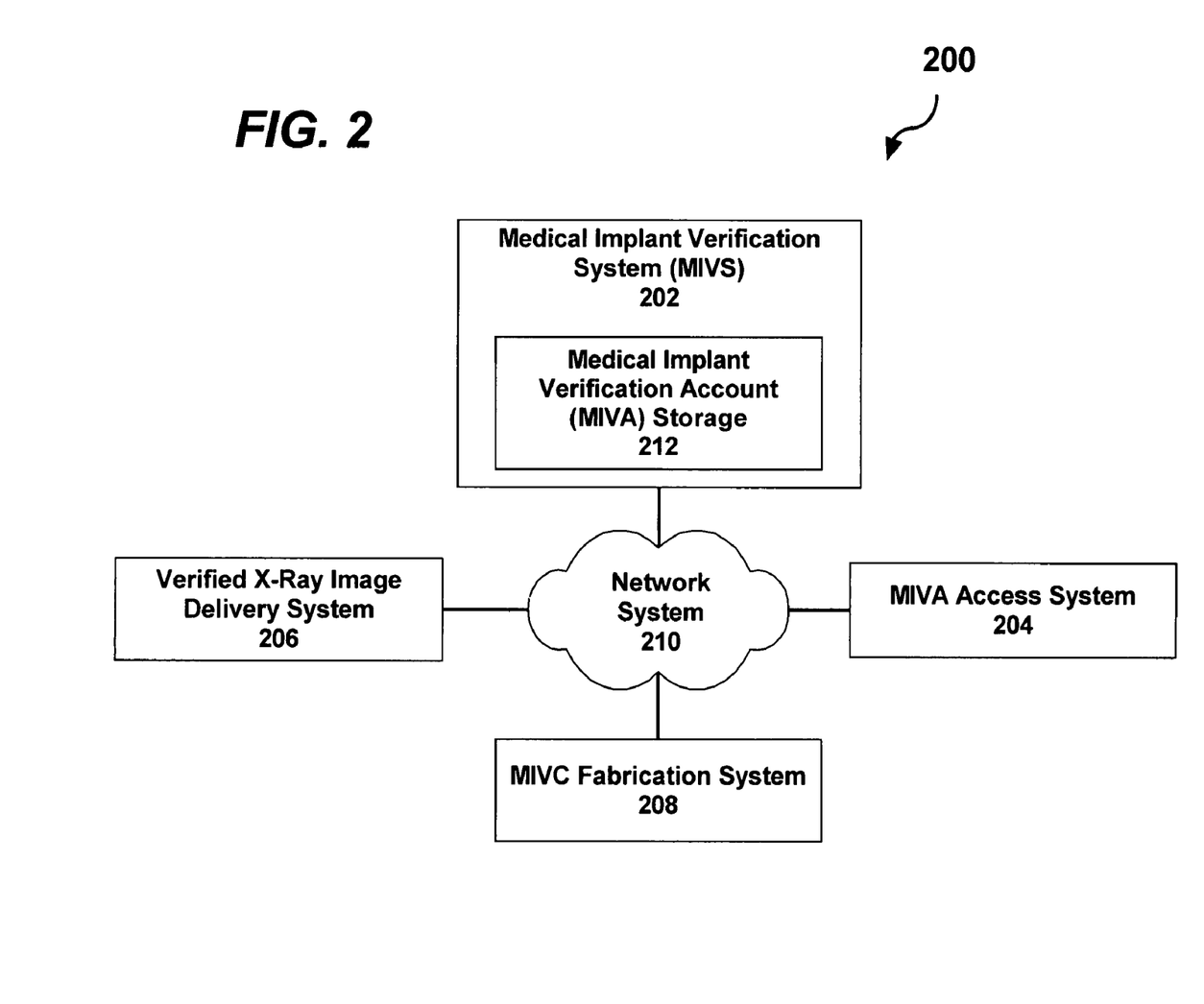
FIG. 2 depicts an apparatus adapted for verifying presence of a medical implant within a patient in accordance with an embodiment of the disclosures made herein.

FIG. 2 depicts an apparatus 200 adapted for verifying presence of a medical implant within a patient in accordance with an embodiment of the disclosures made herein. Specifically, the apparatus 200 is adapted for enabling the method 100 depicted in FIG. 1 to be carried out. The apparatus 200 includes a MIVS 202, a MIVA access system 204, a verified X-ray image delivery system 206, a MIVC fabrication system 208 and a network system 210. The network system 210 is connected between the MIVS 202, the MIVA access system 204, the verified X-ray image delivery system 206 and the MIVC fabrication system 208 for enabling communication therebetween. A public network system such as the Internet is an example of the network system 210. The MIVS 202 includes MIVA storage 212 for storing MIVA information thereon.

The MIVS 202 enables the method 100 to be carried out. A data processing system (e.g., a network server, a mainframe, etc) that is running one or more data processor programs necessary for facilitating the method 100 depicted in FIG. 1 is an example of the MIVS 202. Storage available on a data storage unit, which includes one or more harddrives, is an example of the MIVA storage 212. It is contemplated herein that the MIVS 202 includes a management interface (not shown) for enabling a system administrator to access the MIVS 200.

A data processing system (e.g., a personal computer, a network server, a mainframe or proprietary interface system) running one or more data processor programs for enabling communication with the MIVS is an example of the MIVA access system 204. In practice, it is contemplated that the MIVA access system 204 and a plurality of other MIVA access systems (not shown) are a provided for communication with the MIVS 202 via the network system 210. Such MIVA access systems reside at remote locations from the MIVS 202 (e.g., at airport security check-points, at checkpoints in restricted access facilities, at retail outlet security centers, etc.).

The verified X-ray image delivery system 206 is a system adapted for providing known-authenticated copies of implanted medical implant images to the MIVS 202. A secure and trusted repository of digital X-ray images of implanted medical implants for patients is an example of such a system. The intent of such a system is to serve as a centralized, secure and trusted facility for delivering verified (i.e., known to be authentic) implanted medical implant images to the MIVS 202 in a digital manner over the network system 210. A computer system of a radiologist, physician or the like, which is operated in a controlled-access manner, is another example of the verified X-ray image delivery system 206.

The MIVC fabrication system 208 is a system adapted for receiving MIVC information from the MIVS and facilitating fabrication of MIVC's. An identification card fabrication system of an identification card fabrication vendor is an example of the MIVC fabrication system 208. The intent of such a system is to serve as a centralized, secure and trusted facility for receiving MIVA information from the MIVS 202 and for fabricating MIVC's in accordance with such information.

Figure 3A:
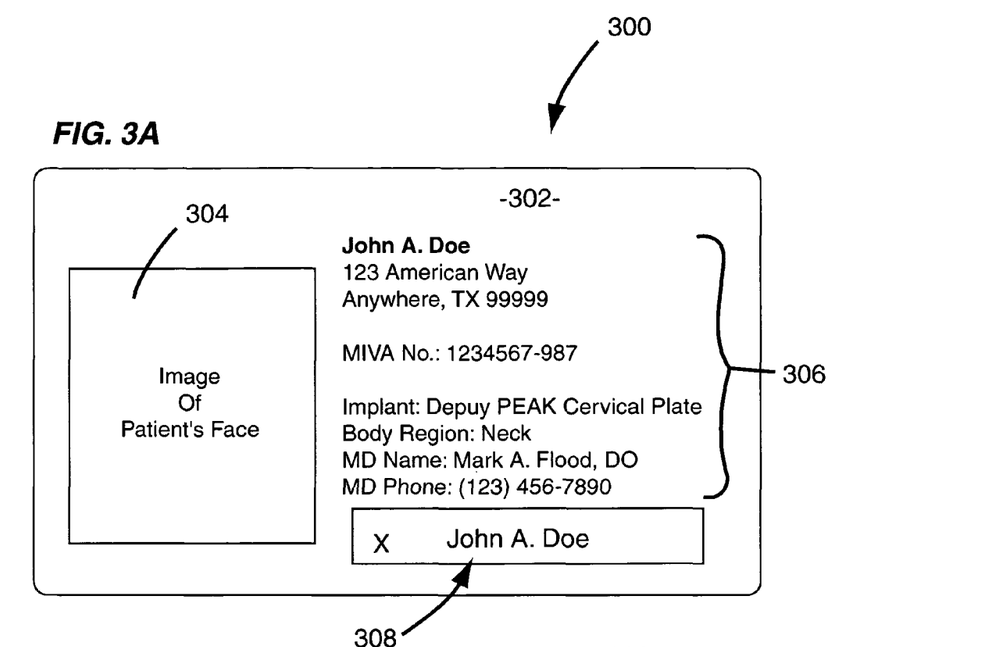
FIG. 3A depicts a first side of a medical implant verification card in accordance with an embodiment of the disclosures made herein.
Figure 3B:
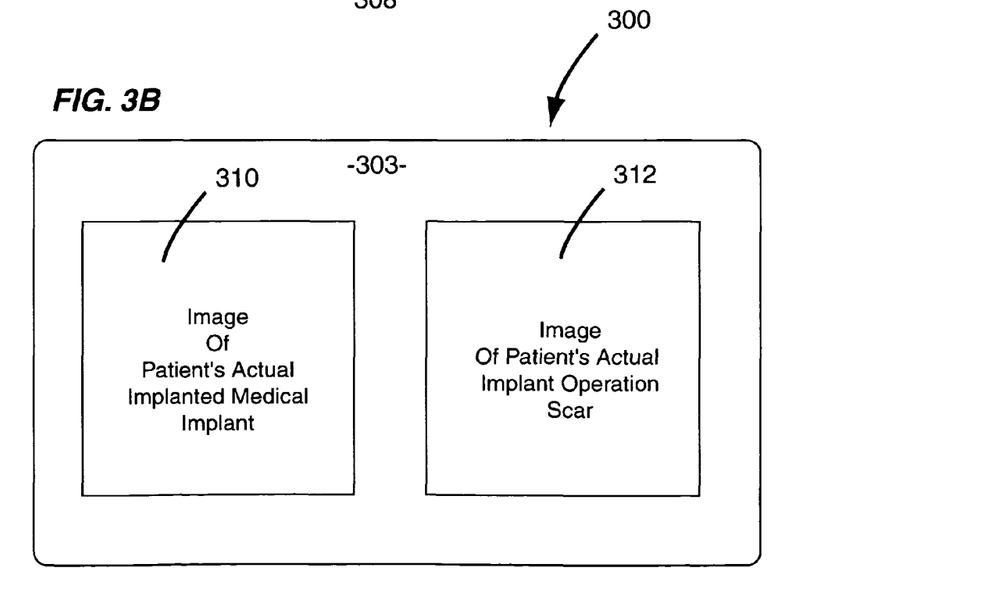
FIG. 3B depicts a second side of a medical implant verification card in accordance with an embodiment of the disclosures made herein.

An embodiment of a MIVC 300 is depicted in FIGS. 3A and 3B. FIGS. 3A and 3B depict a first side 302 and a second side 303, respectively, of the MIVC 300. An image 304 of the patient's face, MIVA information 306 of the patient and a signature 308 of the patient (e.g., a digital reproduction of the patient's actual signature) are provided on the first side 302 of the MIVC 300. Examples of the MIVA information 306 include the patient's name, the patient's address, the patients MIVA number, the make/model of the patient's medical implant, the body region where the medical implant is implanted, the patient's physician, and the physician's phone number.

A brief list of medical implants that include metallic components and that may alert metal detectors include automatic implantable cardiac defibrillators (AICD), bone fusion stimulators, cochlear implants, cranial plates/screws, fracture plates/screws, hip joint replacements, implantable pain pumps, knee joint replacements, metal plates/screws, metallic TMJ implants, oral surgery implants, pacemakers, Parkinson's control systems, podiatry plates/screws, shoulder joint replacements, spinal cord stimulators, spinal implants such as plates/screws/rods/cages, and Vagus nerve stimulators for Epilepsy/seizure disorders. Retained bullet and shrapnel fragments will also alert metal detectors and these patients may also elect to carry the MIVC for verification.

An image 310 of the patient's actual implanted medical implant (i.e., as implanted in the patient's body) and an image 312 of the patient's actual implant operation scar are provided on the second side 303 of the MIVC 300. A high-resolution digital images and a photographic image are examples of the image 304 of the patient's face and the image 312 of the patient's actual implant operation scar. An X-ray image is an example of the image 310 of the patient's actual implanted medical implant. It is contemplated that MIVC's in accordance with embodiments of the disclosures made herein may include one or more measures for reducing the potential for tampering and forgery.

Figure 4:
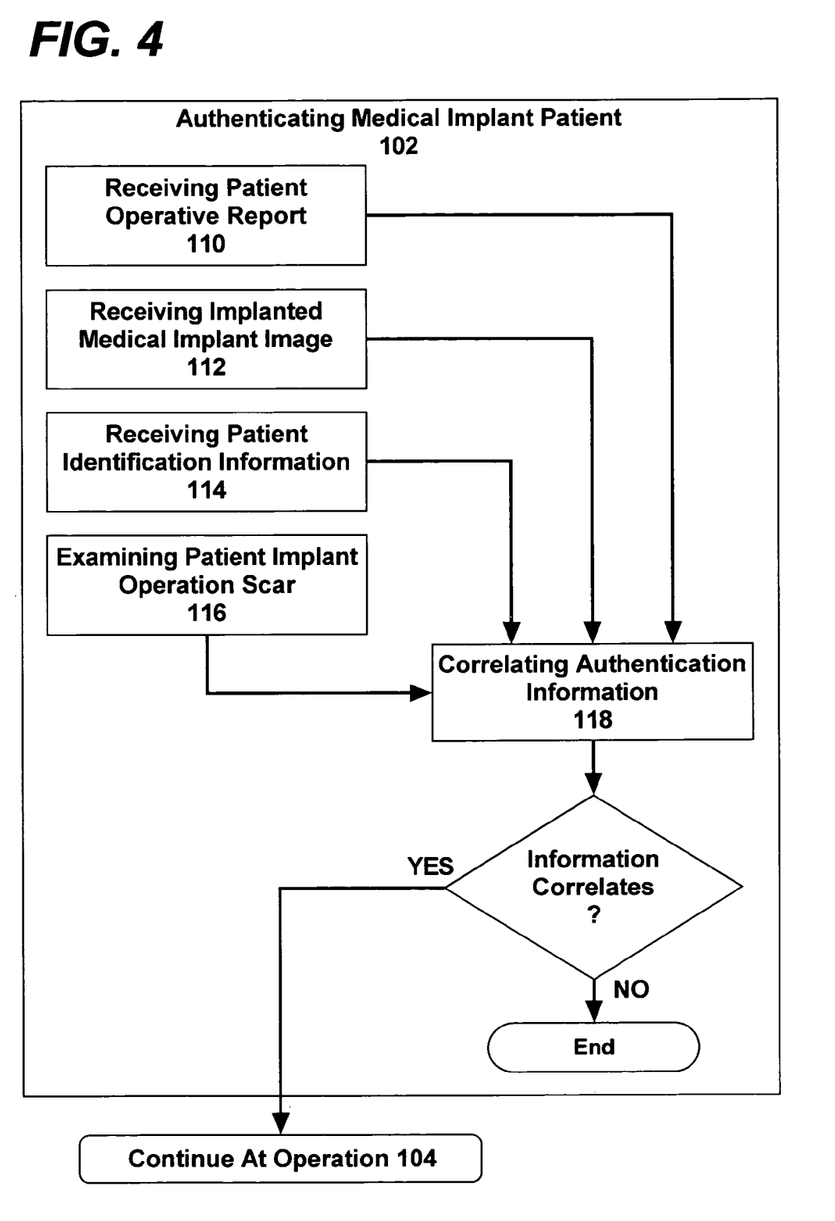
FIG. 4 depicts an embodiment of the operation for authenticating the medical implant patient depicted in FIG. 1.

FIG. 4 depicts an embodiment of the operation 102 for authenticating the medical implant patient. In the depicted embodiment of the operation 102 for authenticating the medical implant patient, a step 110 is performed for receiving a patient operative report, a step 112 is performed for receiving an image (e.g., an X-ray image) showing a medical implant in the patient (i.e. an implanted medical implant image), a step 114 is performed for receiving patient identification information and a step 116 is performed for examining a patient implant operation scar. The patient operative report, the patient implanted medical implant image, the patient identification information and the patient implant operation scar represent examples of authentication information. After receiving the patient operative report, receiving the implanted medical implant image, receiving patient identification information and examining the patient implant operation scar, a step 118 is performed for correlating authentication information. Patient identification information may be correlated against information available on a valid governmental photo ID of the patient (e.g., a driver's license, military ID or passport).

In response to successfully correlating required portions of the authentication information, the patient is thereby authenticated as having a designated medical implant (i.e., an authenticated-patient), the authentication information is verified as being authentic and the method 100 continues at the operation 104 for creating the authenticated-patient MIVA for the medical implant patient. In response to unsuccessfully correlating required portions of the authentication information, the operation 102 ends. It is contemplated herein that at least a portion of the steps of operation 102 may be performed sequentially or in parallel.

Figure 5:
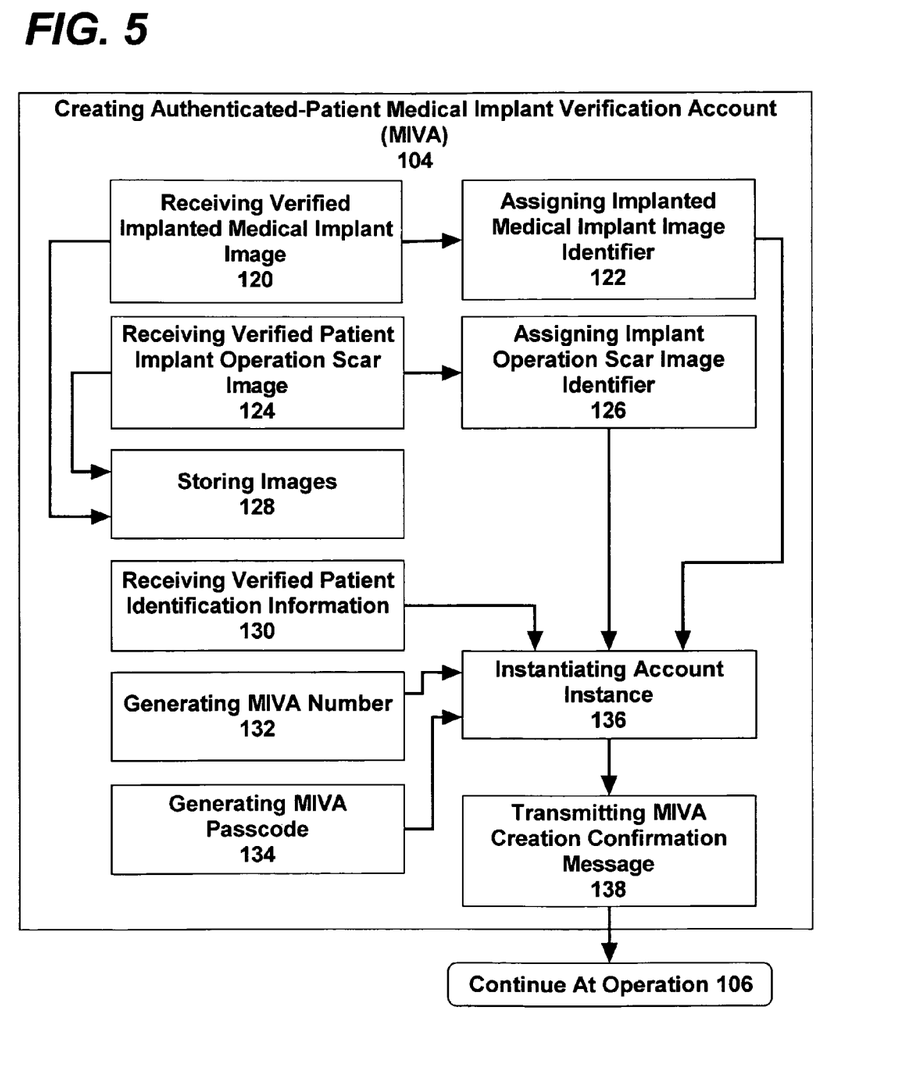
FIG. 5 depicts an embodiment of the operation for creating the authenticated-patient medical implant verification account depicted in FIG. 1.

FIG. 5 depicts an embodiment of the operation 104 for creating the authenticated-patient MIVA. In the depicted embodiment of the operation 104 for creating the authenticated-patient MIVA, a step 120 is performed for receiving a verified implanted medical implant image (e.g., as verified at the operation and then performs 118 in FIG. 4) and then a step 122 is performed for assigning an image identifier (e.g., a file name) to the verified medical implant image. A step 124 is performed for receiving a verified patient implant operation scar image and then performs a step 126 for assigning an image identifier (e.g., a file name) to the verified patient implant operation scar image. In association with assigning the image identifier for the verified implanted medical implant image and assigning the image identifier to the verified patient implant operation scar image, a step 128 is performed for storing the verified medical implant image and the verified patient implant operation scar image.

Still referring to FIG. 5, a step 130 is performed for receiving verified patient identification, a step 132 is performed for generating a MIVA number for the patient (i.e., a system-generated MIVA number) and a step 134 is performed for generating a passcode for the patient (i.e., a system-generated MIVA passcode). It is contemplated herein that the system-generated MIVA passcode may be changed by the patient to another MIVA passcode (i.e., a patient-specified MIVA passcode). As discussed in greater detail below, the MIVA number and the MIVA passcode enable access to the MIVA by the patient and/or authorized representatives of the patient.

After performing the steps (120-134) for receiving, assigning, generating and storing, a step 136 is performed for instantiating an account instance with verified authentication information, the MIVA number, the MIVA passcode and the image identifiers. Instantiating an object in an object environment and populating a record in a database are examples of instantiating an account instance. After instantiating the account instance, a step 138 is performed for transmitting a MIVA creation confirmation message for reception by the patient. Transmitting an e-mail message via the Internet is an example of transmitting the MIVA creation confirmation message. The method 100 then proceeds at the operation 106. It is contemplated herein that at least a portion of the steps of operation 104 may be performed sequentially or in parallel.

Figure 6:
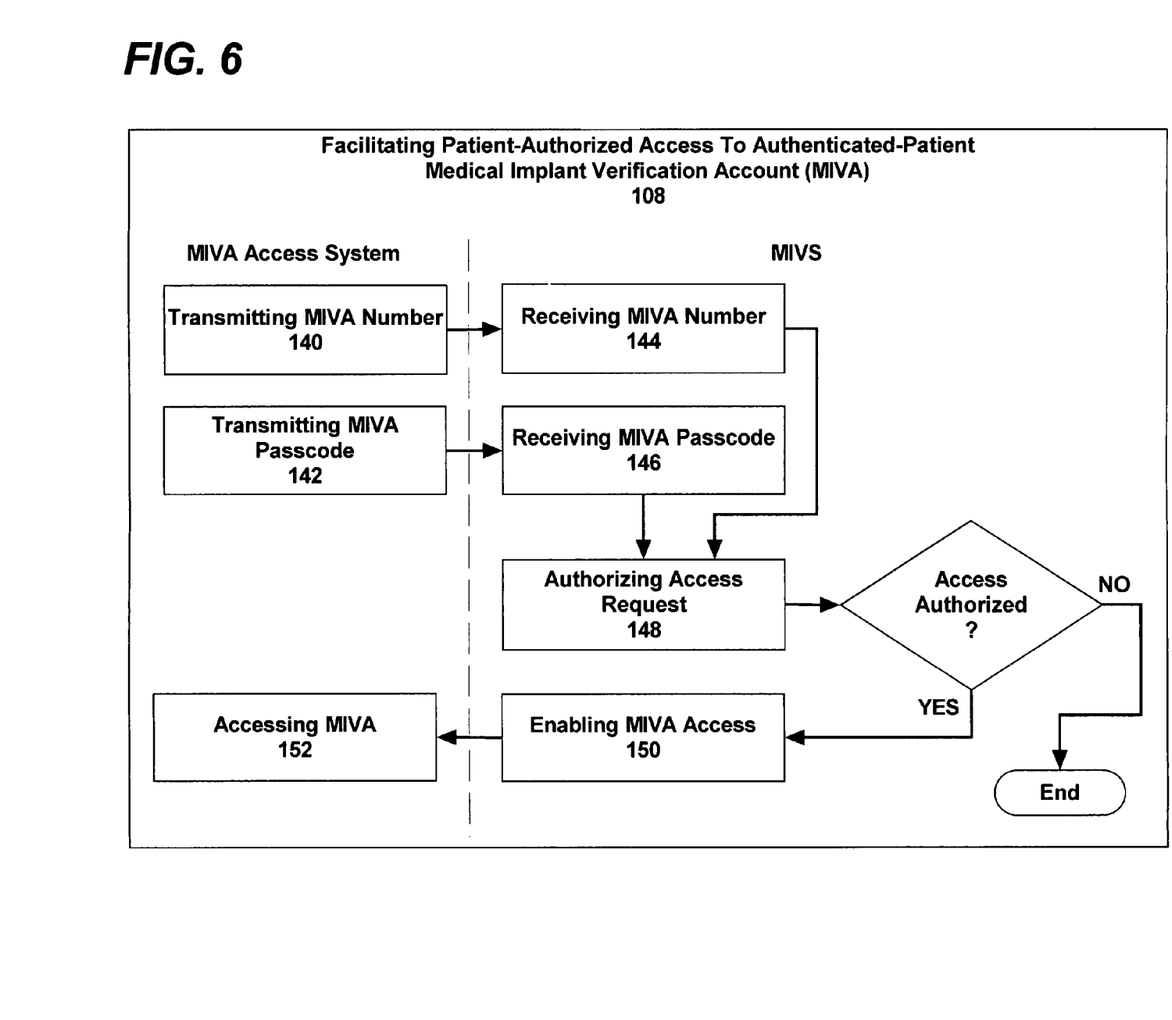
FIG. 6 depicts an embodiment of the operation for facilitating patient-authorized access to the authenticated-patient medical implant verification account depicted in FIG. 1.

FIG. 6 depicts an embodiment of the operation 108 for facilitating patient-authorized access to the authenticated-patient MIVA of a patient. In the depicted embodiment of the operation 108 for facilitating patient-authorized access to the authenticated-patient MIVA of a patient, a MIVA access system performs a step 140 transmitting a MIVA number for reception by a medical implant system (MIVS) and a step 142 for transmitting a MIVA passcode corresponding to the MIVA number for reception by the MIVS. Submission of a MIVA access request comprises transmitting the MIVA number and the MIVA passcode. In response to the MIVS performing a step 144 for receiving the MIVA number and a step 146 for receiving the MIVA passcode, the MIVS performs a step 148 for authorizing the access request. It is contemplated herein that the MIVA number and the MIVA passcode may be transmitted and received sequentially or in parallel.

Still referring to FIG. 6, a step 150 is performed by the MIVS for enabling MIVA access by the MIVA access system in response to the access request being authorized successfully. After the MIVS enables MIVA access, the MIVA access system performs a step 152 for accessing the MIVA. In response to the access request not being authorized successfully, the operation 108 ends without enabling MIVA access to the MIVA access system.

In at least one embodiment of the disclosures made herein, the operation 108 for facilitating patient-authorized access to the authenticated-patient MIVA of a patient is performed over a secure Internet connection. In such an embodiment, the MIVA access system communicates with the MIVS over a secure Internet connection. For example, a MIVS website address is noted on the MIVC, thereby enabling the secure connection to be implemented. Once the secure connection with the MIVS website is established, the party requesting access (i.e., the requesting party) is prompted to enter the patient's MIVA number. Alternatively, the MIVC may be read (e.g., via a magnetic strip) by the MIVA access system.

In response to a valid MIVA number being provided to the MIVS, the requesting party is then prompted for providing a corresponding MIVA passcode. The patient then enters his or her MIVA passcode via a secure means (e.g., a handheld keypad). In response to the corresponding MIVA passcode being entered, access to MIVA information is granted. Without the corresponding MIVA passcode being entered, access to the MIVA is denied.

This MIVS will only provide MIVA information that has been authorized by the patient. It may include the same images that are on the front and/or the back of the MIVC, a full-length image of the patient, a secondary MIVA passcode known only by the patient, etc. Additional information that may be available includes the patient's name, address, DOB, social security number, telephone number, emergency contact's name & telephone number and patient's allergies, blood type and designation as an organ or implant donor. Implant information that may be supplied in the database includes the implanting surgeon's name, address and telephone number, as well as the date of surgery, name of the surgery, implanting hospital's name, address and telephone number, as well as the implant's name and manufacturer and the region of the body where the medical implant resides.

In the preceding detailed description, reference has been made to the accompanying drawings that form a part hereof, and in which are shown by way of illustration specific embodiments in which the invention may be practiced. These embodiments, and certain variants thereof, have been described in sufficient detail to enable those skilled in the art to practice the invention. It is to be understood that other suitable embodiments may be utilized and that logical, mechanical, chemical and electrical changes may be made without departing from the spirit or scope of the invention. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

The invention claimed is:

1. An article of manufacture configured for facilitating verification of an as-implanted medical implant within a patient in possession of the article of manufacture, the article of manufacture comprising:
   a medical implant verification card having a first side and a second side substantially opposite the first side,
   information designating a Medical Implant Verification Account (MIVA) of the patient on at least one of said sides of the medical implant verification card in a manner facilitating said MIVA designating information to be visually inspected by viewing the medical implant verification card;
   an image showing a medical implant as actually implanted within a body of the patient on at least one of said sides of the medical implant verification card in a manner facilitating said implant image to be visually inspected by viewing the medical implant verification card, wherein said medical implant image is an image produced by imaging the medical implant while still implanted within the body of the patient such that a resulting imaged depiction of the medical implant is dependent upon the manner in which the medical implant is implanted within the patient's body; and
   an image of an actual implant operation scar of the patient on one of said sides of the medical implant verification card in a manner facilitating said implant operation scar image to be visually inspected by viewing the medical implant verification card, wherein said implant operation scar image shows a scar on the body of the patient resulting from actual implantation of the medical implant within the body of the patient.

2. The article of manufacture of claim 1 wherein said MIVA designating information includes an account number corresponding to a medical implant verification account of the patient.

3. The article of manufacture of claim 1 wherein:
   said MIVA designating information is on the first side of the medical implant verification card; and said medical implant image is on the second side of the medical implant verification card.

4. The article of manufacture of claim 3 wherein said medical implant image is a reproduction of an X-ray image showing the medical implant as implanted within the body of the patient.

5. The article of manufacture of claim 1 wherein said medical implant image is a reproduction of an X-ray image showing the medical implant as implanted within the body of the patient.

6. The article of manufacture of claim 1 wherein:
   said access enabling information includes an account number corresponding to a medical implant verification account of the patient;
   said access enabling information is on the first side of the medical implant verification card; and
   said medical implant image is on the second side of the medical implant verification card.

7. The article of manufacture of claim 6 wherein said medical implant image is a reproduction of an X-ray image showing the medical implant as implanted within the body of the patient.

8. An article of manufacture configured for facilitating verification of an as-implanted medical implant within a patient in possession of the article of manufacture, the article of manufacture, comprising:
   a medical implant verification card having a first side and a second side substantially opposite the first side,
   information designating a Medical Implant Verification Account (MIVA) of the patient provided on at least one of said sides of the medical implant verification card in a manner facilitating said MIVA designating information to be visually inspected by viewing the medical implant verification card;
   an image showing a medical implant as actually implanted within a body of the patient on one of said sides of the medical implant verification card in a manner facilitating said implant image to be visually inspected by viewing the medical implant verification card, wherein said medical implant image is an image produced by imaging the medical implant while still implanted within the body of the patient such that a resulting imaged depiction of the medical implant is dependent upon the manner in which the medical implant is implanted within the patient's body;
   an image of an actual implant operation scar of the patient on one of said sides of the medical implant verification card in a manner facilitating said implant operation scar image to be visually inspected by viewing the medical implant verification card, wherein said implant operation scar image shows a scar on the body of the patient resulting from actual implantation of the medical implant within the body of the patient; implant identification information designating a type of the medical implant on one of said sides of the medical implant verification card; and
   information designating at least one of a name of a surgeon having performed the operation for implanting the medical implant and information for contacting the surgeon on one of said sides of the medical implant verification card.

9. The article of manufacture of claim 8 wherein said MIVA designating information includes an account number corresponding to a medical implant verification account of the patient.

10. The article of manufacture of claim 8 wherein:
    said MIVA designating information is on the first side of the medical implant verification card; and
    said medical implant image is on the second side of the medical implant verification card.

11. The article of manufacture of claim 10 wherein said medical implant image is a reproduction of an X-ray image showing the medical implant as implanted within the body of the patient.

12. The article of manufacture of claim 8 wherein said medical implant image is a reproduction of an X-ray image showing the medical implant as implanted within the body of the patient.

13. The article of manufacture of claim 8, further comprising:
    information designating a location of the body of the patient at which the medical implant is located on one of said sides of the medical implant verification card.

14. The article of manufacture of claim 13 wherein:
said access enabling information includes an account number corresponding to a medical implant verification account of the patient;
said access enabling information is on the first side of the medical implant verification card; and
said medical implant image is on the second side of the medical implant verification card.

15. The article of manufacture of claim 14 wherein said medical implant image is a reproduction of an X-ray image showing the medical implant as implanted within the body of the patient.

16. An implant verification article configured for facilitating verification of an as-implanted medical implant within a patient in possession of the implant verification article, the implant verification article, comprising:
a medical implant verification card having a first side and a second side opposite, an account number corresponding to a medical implant verification account of the patient on one of said sides of the medical implant verification card;
a reproduction of an X-ray image on one of said sides of the medical implant verification card in a manner facilitating the X-ray image to be visually inspected by viewing the medical implant verification card, wherein the X-ray image shows a medical implant as actually implanted within the body of the patient while such that the imaged depiction of the medical implant within the X-ray image is dependent upon the manner in which the medical implant is implanted within the patient's body;
an image of a face of the patient on one of said sides of the medical implant verification card in a manner facilitating said face image to be visually inspected by viewing the medical implant verification card;
an image of an actual implant operation scar of the patient on one of said sides of the medical implant verification card in a manner facilitating said implant operation scar image to be visually inspected by viewing the medical implant verification card, wherein said implant operation scar image shows a scar on the body of the patient resulting from actual implantation of the medical implant within the body of the patient;
implant identification information on one of said sides of the medical implant verification card in a manner facilitating said implant identification information to be visually inspected by viewing the medical implant verification card, wherein said implant identification information designates a type of the medical implant; and
surgeon contact information on one of said sides of the medical implant verification card, wherein said surgeon contact information includes a name of a surgeon having performed the operation for implanting the medical implant and a phone number for contacting the surgeon.

17. The implant verification article of claim 16 wherein:
the image of the face of the patient is on a first side of the medical implant verification card; said X-ray image is on a second side of the medical implant verification card; and said implant operation scar image is on the second side of the medical implant verification card.

18. The implant verification article of claim 17, further comprising:
information on one of said sides of the medical implant verification card designating a location of the body of the patient at which the medical implant is located.

* * * * *